United States Patent
McIntyre

(10) Patent No.: US 7,931,029 B2
(45) Date of Patent: Apr. 26, 2011

(54) METHOD AND APPARATUS FOR UTERUS STABILIZATION

(75) Inventor: Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 530 days.

(21) Appl. No.: 11/089,787

(22) Filed: Mar. 25, 2005

(65) Prior Publication Data

US 2006/0213526 A1  Sep. 28, 2006

(51) Int. Cl.
*A61B 19/00* (2006.01)

(52) U.S. Cl. .......................... 128/898; 604/113; 424/422

(58) Field of Classification Search .................. 128/897, 128/898; 424/78.08, 78.37, 422, 484, 486; 604/113, 183, 247, 364, 506; 606/1, 193
See application file for complete search history.

(56) References Cited

U.S. PATENT DOCUMENTS

| | | | |
|---|---|---|---|
| 3,996,921 A | 12/1976 | Neuwirth et al. | |
| 5,372,584 A * | 12/1994 | Zink et al. | 604/515 |
| 5,431,639 A * | 7/1995 | Shaw | 604/264 |
| 5,752,974 A * | 5/1998 | Rhee et al. | 606/214 |
| 5,928,249 A * | 7/1999 | Saadat et al. | 606/119 |
| 6,306,177 B1 * | 10/2001 | Felt et al. | 623/23.6 |
| 6,395,012 B1 | 5/2002 | Yoon et al. | |
| 6,605,294 B2 * | 8/2003 | Sawhney | 424/426 |
| 6,610,033 B1 * | 8/2003 | Melanson et al. | 604/181 |
| 6,663,594 B2 | 12/2003 | Sahatjian et al. | |
| 6,689,148 B2 * | 2/2004 | Sawhney et al. | 606/193 |
| 2005/0033163 A1 | 2/2005 | Duchon et al. | |

* cited by examiner

*Primary Examiner* — John P Lacyk
(74) *Attorney, Agent, or Firm* — Fay Kaplun & Marcin, LLP

(57) ABSTRACT

A system and method for surgery on a hollow organ comprises a source of a biocompatible gellable fluid in a flowable state and an insertion device for introducing the gellable fluid into a hollow organ of a patient, the gellable fluid transitioning from the flowable state to a gel-like state to form a gel mass within the hollow organ to support a wall of the hollow organ in combination with a state control apparatus for transitioning the gel mass from the gel-like state to the flowable state and a removal device for removing from the hollow organ the gellable fluid in the flowable state.

8 Claims, 1 Drawing Sheet

METHOD AND APPARATUS FOR UTERUS STABILIZATION

BACKGROUND OF THE INVENTION

The treatment of many diseases affecting hollow organs or other body lumens often requires direct surgical treatment of the wall of the organ. Tumors, fibroids, lesions and other conditions affecting the walls of hollow organs are generally treated surgically using tools that may be inserted into the organ, or which reach the surface of the organ from the outside. These tools may be used to deliver electric energy, heat or a chemical ablation compound to necrose the targeted tissue, or may simply be used to cut the diseased tissue from surrounding healthy tissue.

One difficulty associated with these procedures is that the walls of most hollow organs are not fixed firmly in place but are relatively free to move, flex and shift position. Thus, when a force is applied to such tissue, (e.g., by a cutting or ablating tool pressed thereagainst), the target area moves making it difficult to complete the operation. For example, during procedures to treat uterine fibroids such as myomectomies and myolysis, the fibroids as well as the uterine wall move around making it difficult to grasp or prevent movement of the affected tissue complicating and lengthening the procedure.

Various methods have been devised in an attempt to stabilize the uterus wall during surgery. Screw-like devices have been attached to the target tissue to retain it in place while another tool is used to ablate the tissue. However, these screw-like devices must be sufficiently small to fit through endoscopic or laparoscopic instruments such as trocars reaching the target tissue, and thus may not be able to grasp enough tissue to fully stabilize the target region. Manipulator devices of various kinds may be used to move the target organ, but generally these devices cannot provide stability to the entire organ, and the surgeon still has to face a target tissue which is difficult to grasp and hold.

SUMMARY OF THE INVENTION

In one aspect, the present invention is directed to a surgical system comprising a source of a biocompatible gellable fluid in a flowable state and an insertion device for introducing the gellable fluid into a hollow organ of a patient, the gellable fluid transitioning from the flowable state to a gel-like state to form a gel mass within the hollow organ, the gel mass supporting walls of the hollow organ to stabilize the walls in combination with a first state control apparatus for transitioning the gel mass from the gel-like state to the flowable state and a removal device for removing from the uterus the gellable fluid in the flowable state.

In a further aspect, the present invention is directed to a method of performing surgery, comprising inserting into a hollow organ a gellable fluid and causing a transition of the gellable fluid from substantially flowable state to a substantially gel-like state to form a gel mass supporting a wall of the hollow organ in combination with surgically treating the wall of the hollow organ, causing a transition of the gellable fluid of the gel mass to the substantially flowable state and removing the gellable fluid from the hollow organ.

DETAILED DESCRIPTION

Figure 1:
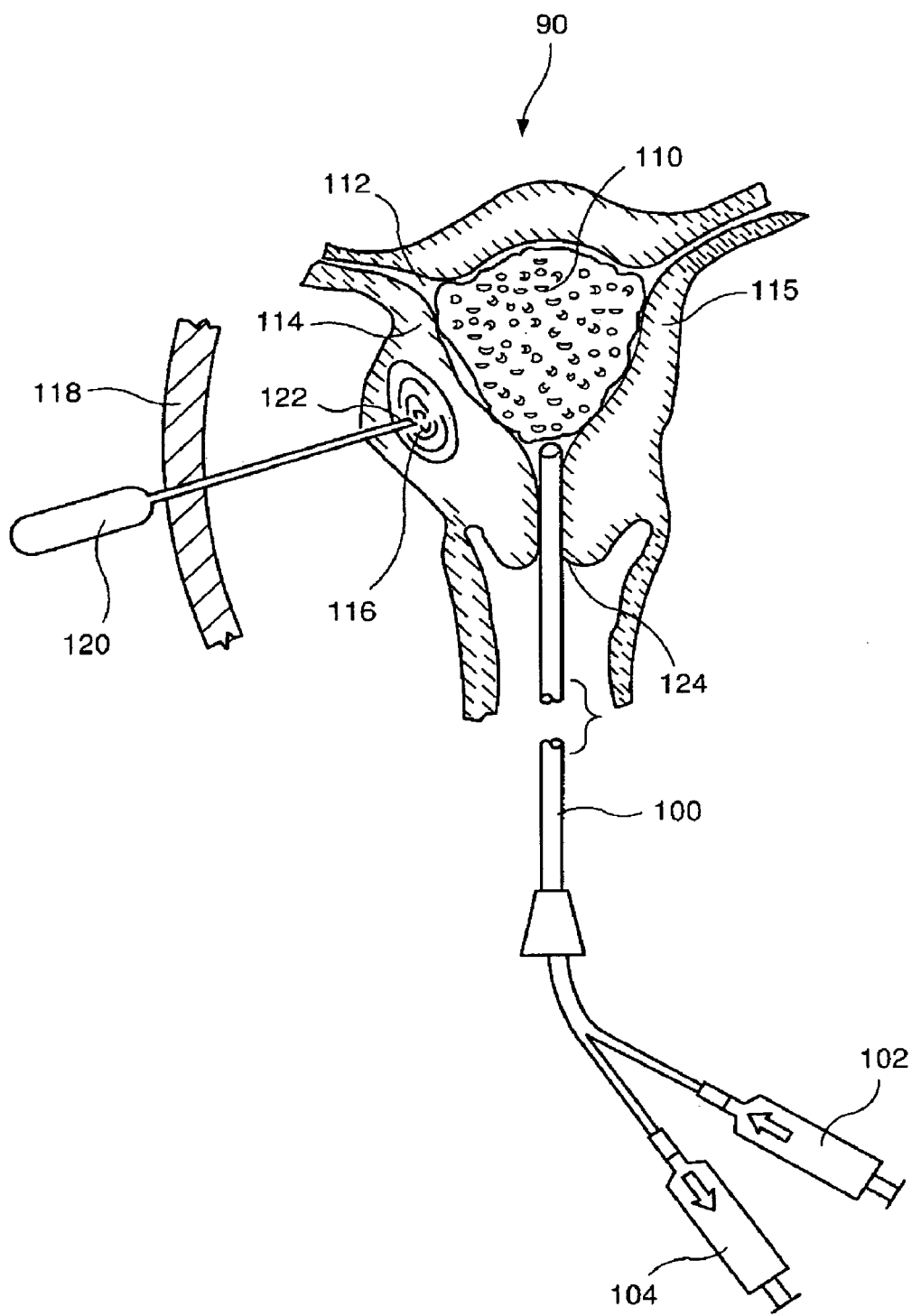
FIG. 1 is a schematic diagram showing an exemplary embodiment of the system according to the invention, including a gellable material inserted into an uterus.

The present invention may be further understood with reference to the following description and the appended drawings, wherein like elements are referred to with the same reference numerals. The present invention is related to methods and systems to stabilize a hollow organ during surgery. More specifically, the invention is directed to methods and systems for stabilizing the uterus during surgery to treat fibroids or other abnormalities of the wall of the uterus.

As described above, surgical procedures carried out on hollow organs present special problems because the associated tissues can be moved by a small amount of pressure or force. For example, in procedures such as myomectomies and myolysis, this movement makes grasping and/or piercing a fibroid to apply a source of RF or thermal energy, or other tissue ablation device thereto more difficult. Surgical removal of the tissue by cutting with a blade is also made more difficult as the uterine wall moves away from the blade without offering sufficient resistance thereto.

Devices used to resolve these shortcomings include fibroid screws, tumor screws and various organ manipulation tools. Fibroid and tumor screws are designed to 'bite' into the target tissue and retain it in place while another medical device, generally a tissue ablation probe, is used to puncture the tissue mass and apply an ablative treatment thereto. The tumor screws are typically inserted into the body via a laparoscope, endoscope or other similar instrument, and therefore have to be sufficiently small to fit through the working passage of those instruments. The small size of the screws prevents them from grasping a large amount of tissue, so that only a small amount of diseased tissue is immobilized or stabilized in the procedure. In addition, the screw's small size makes it more likely that it will pull free of the target tissue necessitating a repeat of the procedure.

Organ manipulation devices are inserted in the patient's body and are used to move the organ being treated in a position favorable to facilitate the surgical procedure. These devices are generally spoon-like or forceps-like elongated tools. However, this type of organ manipulation device generally does not completely fill the cavity of the hollow organ into which it is inserted. Thus, these devices are unable to stabilize the entire organ and piercing the target tissue with an ablation probe may still be difficult even when an organ manipulation device is used.

According to exemplary embodiments of the present invention, a hollow organ such as the uterus is stabilized in preparation for surgery by injecting a flowable material, typically a fluid, into the cavity of the hollow organ. Once inside the organ, the flowable fluid is transitioned to a gel-like state, so that the cavity is filled with a resilient mass, stabilizing the cavity during surgical procedures by providing a backing behind the wall of the hollow organ against which the surgeon may push.

After the therapy has been completed, the gel-like substance is transitioned back to a flowable state for removal from the organ. As would be understood by those skilled in the art, different drainage and/or aspiration devices may be used to remove the flowable fluid from the organ. For example, an endoscope or similar device incorporating aspiration lumens may be used. The fluid utilized may use different mechanisms to change state, but generally must be gellable under specifiable conditions compatible with the environment in which it is to be used. The fluid should be in a substantially liquid, flowable state when inserted and withdrawn from the hollow organ, and should be solidifiable into a gel-like, non flowing state during the surgical procedure.

Using a gellable fluid inside the cavity of the target organ, according to embodiments of the present invention, renders surgical procedures performed on those organs safer and faster, by providing increased stability and a more fixed position of the target tissue.

According to one exemplary embodiment, stabilization of the uterus is carried out by inserting a gellable fluid into the uterine cavity through an hysteroscope. FIG. 1 shows a schematic view of an apparatus for use in performing the procedure according to the present invention. In this example, a hysteroscope 100 is used to treat a patient's uterus 90. More specifically, a uterine fibroid 116 present on a wall 114 of the uterus 90 is to be treated surgically. In this example, a myolysis probe or injection needle 120 is used to reach the tissue of the uterine fibroid 116 through the patient's skin 118. Conventionally, when the distal tip 122 of the probe 120 starts pushing against the fibroid 116, the uterine wall 114 offers little resistance and moves out of the way, together with the fibroid 116. This makes it very difficult for the sharp distal end 122 to pierce the fibroid's tissue.

According to the invention, stabilization of the uterus 90 is achieved by injecting a fluid into the uterine cavity 112, and causing the fluid to transition from a flowable state to a gel-like state before performing the surgical procedure to treat the fibroid 116. For example, a single or dual lumen hysteroscope 100 may be used to insert the gellable material through the cervix 124 and into the uterine cavity 112. The hysteroscope 100 may include a fluid supply component 102, such as a syringe or other source of pressurized fluid. The fluid supply component 102 may be hand operated, or may use other mechanisms as known in the art to propel the fluid into the uterus 90 at an appropriate pressure. Fluid should be supplied to the uterus 90 until intrauterine pressure is between 10 and 50 mmHg (uterine volumes 15-45 cc).

The gellable fluid inserted into the uterine cavity 112 may, for example, be a lower critical solution (LCST) material which changes from a flowable state to a gel-like state when moving past a critical temperature. For example, the fluid may be liquid below the critical temperature, and may be gel-like above that temperature. If the critical temperature is selected to be just below the body temperature, the fluid may be cooled before injection into the body so that, after injection, the fluid is warmed by body heat above its critical temperature to transition to the gel-like state, forming a mass 110 within the uterine cavity 112. Examples of fluids that may be used for this purpose include polyoxyethylene-polyoxypropylene (PEO-PPO) block copolymers, such as Pluronic acid F127 and F108. It will be apparent to those of skill in the art that additional compounds may be used, within the requirement of being biocompatible and having a critical temperature substantially equal to or slightly below the body temperature. The critical temperature is preferably within 10-37 degrees C. Once the gellable fluid has been introduced into uterus 90, an appropriate procedure to cause the fluid to gel is performed. For example, the procedure may consist of simply letting a pre-cooled fluid warm to the body temperature within the uterus 90 until the critical temperature is exceeded. This process is suitable for LCST fluids, as described above. Of course, those skilled in the art will understand that the fluid may be warmed to speed the formation of the mass 110.

In another embodiment, the gellable fluid may be a cross-linkable polymer which is a fluid when not cross linked, and becomes a gel when exposed to a cross linking agent. In this exemplary embodiment, the gellable fluid containing the cross-linkable polymers is inserted into the uterine cavity 112, for example through a hysteroscope as described above. Once the fluid is in place, a cross linking agent is introduced, also for example through the working lumen of the hysteroscope or other device. The reaction of the two compounds causes the fluid to become gel-like and form the mass 110. A variety of cross linkable polymers may be used according to the invention, such as ionically and non-ionically cross-linkable polymers. It will be apparent to those of skill in the art that many biocompatible, cross-linkable polymers and cross-linking catalytic agents may be used according to the invention. The particular compound to be used may be selected in view of the desired fluid and gel-like properties which may be obtained, and based on the surgical procedure to be performed. Additional gellable fluids and methods of transitioning the selected fluid to a gel-like state may be used, as will be apparent to those of skill in the art.

Additional elements may be included in the gellable fluid that is introduced into the cavity of the hollow organ. For example, various therapeutic compounds may be added to the basic gellable fluid. Drugs which assist in the treatment of the lesion or fibroid may be included (GNRH's for example), as well as chemotherapy agents, disinfecting agents, etc. Analgesic drugs may also be included, to reduce the discomfort to the patient caused by the surgery. To facilitate certain procedures, radiopaque materials such as sodium bicarbonate, barium sulfate and others known in the art may be included in the gellable fluid, to simplify visualization of the organ being treated.

After the fluid has been filled into the uterine cavity 112 and formed into a gel-like mass 110, the wall 114 of the uterus 90 becomes more stable facilitating treatment of fibroids and other growths and lesions. In addition, the gel-like mass 110 also prevents the wall 114 from being pushed too close to the opposite wall 115 of the uterus 90, increasing the safety of certain procedures that involve piercing or cutting the tissue of a fibroid 116 with a sharp point, such as tip 122. By retaining a substantially fixed distance between the opposed walls 114, 115 it is less likely that the sharp point 122 will reach the opposite wall 115 and cause an unwanted perforation thereof.

After treatment has been completed, the gel-like material may be removed from the uterine cavity 112. In the case of a gellable fluid of the LCST type, the fluid in the gel-like state is transitioned back to the fluid state by cooling it below the critical temperature. In one exemplary embodiment, a fluid cooler than the critical temperature is injected into the uterus 90 in the same manner as the gellable fluid was injected to bring the temperature of the mass 110 back below the critical temperature at which point it returns to the liquid state for aspiration from the uterus 90. For example, a hysteroscope 100 may be used, and more specifically a single or dual lumen device placed in the uterus 90 through the working channel of the hysteroscope 100 is used to introduce the cooling fluid thereto.

If a cross-linkable polymer is used as the gellable fluid, a de-cross linking agent os injected into the uterus 90 after completion of the procedure. The de-cross linking agent returns the gel-like mass 110 to a substantially liquid state for removal from the uterine cavity 112. As in the case of a LCST fluid, the working channel of a hysteroscope or other device inserted through the hysteroscope may be used to remove the flowable material. In some cases, it may be beneficial to use a single or multi lumen device that fits in the working lumen of the hysteroscope and which is better suited to receive the flow of fluid being removed. A suction device 104, such as a syringe or other hand operated or powered device may be used to facilitate removal of the fluid from the cavity of the hollow organ. A catheter, cannula or other device may be used, for example, to allow extraction of the fluid by gravity, or by applying an external force to the fluid.

The present invention has been described with reference to specific embodiments, and more specifically to a method and system to treat uterine fibroids. However, other embodiments may be devised that are applicable to other types of diseases and to other hollow organs, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A method of performing surgery, comprising:
    inserting into a hollow organ a gellable fluid in a flowable state;
    causing a transition of the gellable fluid from substantially flowable state to a substantially gel-like state to form a gel mass supporting a wall of the hollow organ;
    surgically treating the wall of the hollow organ;
    causing a transition of the gellable fluid of the gel mass to the substantially flowable state by introducing a transition agent into the patient through a first device inserted in the hollow organ; and
    removing the gellable fluid from the hollow organ via the first device, wherein the organ is a uterus, and an amount of the gellable fluid inserted into the uterus is sufficient so that the gel mass maintains a substantially fixed distance between opposed walls of the uterus.

2. The method according to claim 1, wherein a quantity of gellable fluid inserted into the hollow organ is selected so that, when the fluid is transitioned to the gel-like state, the gel mass formed maintains a substantially fixed distance between opposite portions of the wall during the surgical treatment of the wall.

3. The method according to claim 1, wherein the surgical treatment of the wall includes one of a myolysis, a myomectomy, an injection and an ablation procedure.

4. The method according to claim 1, wherein the gellable fluid is a cross-linkable polymer, the method further comprising inserting a cross linking agent into the hollow organ to transition the gellable fluid to the gel-like state.

5. The method according to claim 4, wherein the fluid is a LCST, further comprising inserting a de-cross linking agent into the hollow organ after completion of the surgical treatment and prior to removal of the gellable fluid therefrom to transition the gellable fluid back to the flowable state.

6. The method according to claim 1, further comprising cooling the gellable fluid to a temperature lower than the critical temperature to transition the gellable fluid from the gel-like state to the flowable state prior to removal thereof from the hollow organ.

7. The method according to claim 1, wherein the hollow organ is a uterus, further comprising inserting into the uterus a hysteroscope adapted to inject fluids thereto.

8. The method according to claim 1, wherein gellable fluid is inserted into the uterus to a pressure not exceeding 50 mmHg.

* * * * *